United States Patent [19]

Ringrose

[11] Patent Number: 4,793,973

[45] Date of Patent: Dec. 27, 1988

[54] CONTAINER FOR ADDING ANTIBODIES OR ANTIGENS TO A BIOLOGICAL LIQUID

[75] Inventor: Anthony Ringrose, Chene-Bougeries, Switzerland

[73] Assignee: Serono Diagnostic Partners, Braintree, Mass.

[21] Appl. No.: 120,742

[22] Filed: Nov. 12, 1987

Related U.S. Application Data

[63] Continuation of Ser. No. 882,344, Jul. 7, 1986, abandoned.

[30] Foreign Application Priority Data

Jul. 8, 1985 [CH] Switzerland .......................... 2956/85

[51] Int. Cl.⁴ ....................... G01N 21/07; G01N 33/48
[52] U.S. Cl. ...................................... 422/102; 422/58;
422/72; 422/73; 436/810; 366/114; 73/864.91
[58] Field of Search .................... 422/72, 73, 102, 61,
422/55, 58; 436/178, 809, 810; 435/296, 299,
300; 366/113, 114 X, 115; 73/864.91 X;
206/569

[56] References Cited

U.S. PATENT DOCUMENTS

| | | | |
|---|---|---|---|
| 3,288,318 | 11/1966 | Corbin et al. | 422/102 |
| 3,730,489 | 5/1973 | Morita | 366/113 |
| 3,937,236 | 2/1976 | Runnells | 366/114 |
| 4,074,976 | 2/1978 | Gower et al. | 422/102 |
| 4,106,907 | 8/1978 | Charlton et al. | 436/810 |
| 4,229,104 | 10/1980 | Lahme et al. . | |
| 4,238,323 | 12/1980 | Zakharova et al. . | |
| 4,239,853 | 12/1980 | Bradley | 422/72 |
| 4,298,478 | 11/1981 | Watson et al. . | |
| 4,371,498 | 2/1983 | Scordato et al. | 422/102 |
| 4,387,992 | 6/1983 | Swarz . | |
| 4,391,780 | 7/1983 | Boris | 422/102 |
| 4,457,894 | 7/1984 | Clark et al. | 422/73 |

FOREIGN PATENT DOCUMENTS

| | | | |
|---|---|---|---|
| 100664 | 2/1984 | European Pat. Off. | 422/102 |
| 2915145 | 10/1979 | Fed. Rep. of Germany | 422/102 |

Primary Examiner—Barry S. Richman
Assistant Examiner—Lynn M. Kummert
Attorney, Agent, or Firm—Ostrolenk, Faber, Gerb & Soffen

[57] ABSTRACT

A container for determining antibodies or antigens in a biological liquid by the formation of specific antibody-antigen complexes, in which one partner element is initially associated with suspended magnetic particles that are subsequently regrouped against a collecting area of a first side wall of the container when the container is positioned within a magnetic field that extends through that area of the side wall. To prevent the particles from sliding down when the magnetic field is eliminated and to allow effective pipetting, the lower part of the side wall is adjacent to a planar surface formed at an obtuse angle to said side wall and tangent to a concave bottom surface that is itself tangent to a second side wall of the container located opposite to the first side wall.

5 Claims, 1 Drawing Sheet

CONTAINER FOR ADDING ANTIBODIES OR ANTIGENS TO A BIOLOGICAL LIQUID

This is a continuation of application Ser. No. 882,344, filed on July 7, 1986, now abandoned.

BACKGROUND OF THE INVENTION

The present invention concerns a container for measuring antibodies or antigens in a biological liquid by creating specific antibody-antigen complexes, in which one element of the complex is initially associated with suspended magnetic particles that are subsequently regrouped against a certain area of one wall of the container when the container is positioned within a magnetic field that extends through that area of the wall.

In a known method of adding antibodies or antigens to a biological liquid, liquid magnetic particles associated with either antigens or antibodies specific to the respective antibodies or antigens that are to be ascertained are added to the liquid in sufficient excess to ensure that all the antibodies or antigens to be measured will combine with a respective antigen or antibody specific to them. The magnetic particles are then attracted to one wall of the container and all substances except the magnetic particles associated with their specific antigen or antibody reactant combined or uncombined with their respective antibody or antigen partner are evacuated from the container. The container is then rinsed out and a reaction liquid is introduced to create an enzymatic reaction with the antibodies or antigens. The particles are suspended in the liquid for a prescribed period and an agent is added to the liquid to terminate the reaction. Finally, magnetic particles are again attracted to the one wall of the container and the reaction liquid is measured colorimetrically.

Attracting the magnetic particles to the bottom of a dish and evacuating the biological liquid by turning the dish upside down along with the magnet, which would then maintain the particles against the bottom, has already been proposed. This procedure, however, is not very practical. Turning a dish upside down inside automatic analysis equipment necessitates a large number of mechanisms. It is also necessary to make provisions for collecting the liquid that spills out of the dishes.

One variation of the proposed method involves positioning the magnet at one side of the dish to attract the magnetic particles to a certain area of the wall. The bottom of the dish takes the form of a spherical cap which is tangent to a tubular body in the case of a dish with a circular cross-section or by a cavity with a straight generatrix which is parallel to two opposing faces of the tubular body and tangent to the faces in the case of a dish with a rectangular cross-section. The bottom walls that are tangent to the tubular section of the dish are intended to promote stirring of the liquid and to prevent dead zones which remain stationary during agitation thereby making the mixture non-homogeneous. The drawback to a dish bottom of this particular shape is that the magnet that attracts the magnetic particles to a certain area of the wall has to be constantly retained at that area in order to maintain them against the wall. This makes it necessary to provide one magnet for each dish as well as means for shifting the magnet between an active and an inactive position. When the magnet is part of automatic analysis equipment in which the dishes are transported from one operating point to another by a conveyor, it must be part of the conveyor. Such a solution is complicated and hence expensive. If the magnets are positioned only along the sections of the path of the conveyor within which the magnetic particles are to be attracted to the particular portion of the wall of the dish, the particles will slide farther along the wall every time the conveyor shifts the dish from one magnet to the next and will eventually arrive more or less at the bottom of the dish. Inasmuch as the whole method of collecting the magnetic particles within a certain area of the wall of the dish is intended to allow evacuation of the liquid with a pipette, some of the particles that slide down to the bottom will also be evacuated and will inadmissibly contaminate the measurement results.

BRIEF DESCRIPTION OF THE INVENTION

The object of the present invention is to at least to some extent eliminate the drawbacks of the aforesaid methods.

This object is attained in accordance with the invention in an improved container for adding antibodies or antigens.

The advantage of this container is that a portion of the bottom wall of the container is formed at an obtuse angle to one side wall of the dish so as to be fairly close to the horizontal and defines a retaining surface which briefly prevents the collected magnetic particles from sliding when they are released from the effect of the magnetic field. Furthermore, since the oblique face is tangent to a concave area of the bottom wall that is itself tangent to the side wall of the container located opposite the first side wall, the shape of the bottom wall of the container does not allow dead zones while the liquid is being mixed because the shape will essentially coincide with the rounded shape of the dish. A dish bottom of this shape will allow pipetting below the level at which the particles are collected, and both the biological liquid and the rinse can be evacuated from the container.

BRIEF DESCRIPTION OF THE DRAWINGS

One embodiment and a variant of the invention will now be described with reference to the attached drawing, in which.

DETAILED DESCRIPTION OF THE PREFERRED EMBODIMENTS

Figure 1:
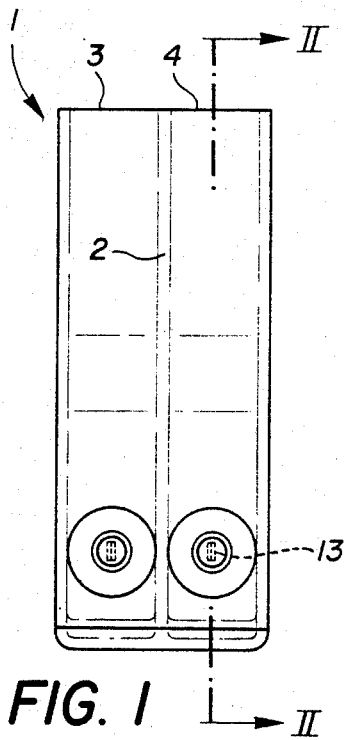
FIG. 1 is a front view of a container in accordance with the invention.
Figure 2:
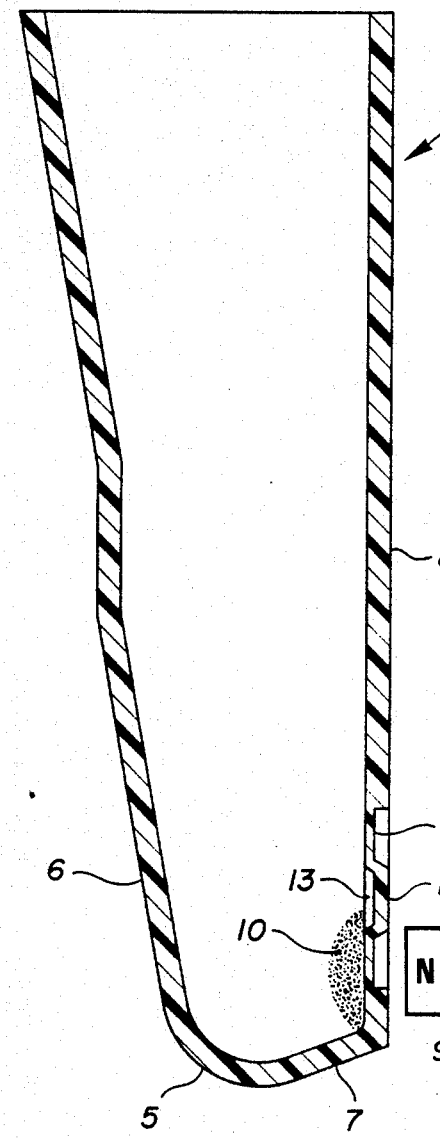
FIG. 2 is a section along the line II—II in FIG. 1.

Referring now to the drawings where like numerals indicate like elements, there is shown in FIGS. 1 and 2 a container constructed in accordance with the principles of the invention and designated generally as container 1. Container 1 is divided by a partition 2 into two compartments 3 and 4 that are rectangular in cross-section and taper slightly upwardly and outwardly as shown in FIG. 2. One compartment is intended to accomodate a sample to be analyzed along with its appropriate reagent or reagents and the other is intended to accomodate a control substance that functions as a reference for the particular test being conducted along with its appropriate reagent or reagents. The invention is obviously not restricted to an embodiment employing only two compartments.

It will be evident from FIG. 2 that the shape of the bottom wall of the container is not an arc of a circle which is tangent to two opposing lateral faces as in all other analysis containers of this type. Rather, the shape is intended to prevent the establishment of dead zones while the liquid is being agitated. The cross-section of the bottom wall is an arc 5 of a circle that, while it is tangent to one lateral face 6 of the container, is not tangent to the opposite lateral face but rather is tangent to an oblique face 7 that is itself at an obtuse angle to the opposite lateral face 8.

The area of opposite lateral face 8 that is adjacent to and forms an obtuse angle with oblique face 7 is intended to be positioned opposite a permanent magnet 9. The magnet collects the magnetic particles 10 suspended within compartments 3 and 4 for the purpose specified previously herein. The particular obtuse angle between faces 7 and 8 in the illustrated embodiment is 110°. The closer the angle is to 90° the more the particles will be retained against the base of opposite lateral face 8, although, if the angle were exactly 90°, the bottom of the container and the lower part of the area that the particles collect in would be at the same level. Furthermore, the closer the angle is to 90° the greater the risk of a dead zone while the liquid is being agitated. It is, rather, preferable as previously discussed herein, for the point of the pipette to arrive below the lower part of the area that the particles collect in. In practice, the angle between faces 7 and 8 is preferably between 105° and 120°.

The area of the lateral face 8 that magnetic particles 10 are supposed to collect in approximately coincides with an area of the wall of each compartment 3 and 4 that is provided with a depressed annular surface 11 (FIG. 2) surrounding a circular area 12 as thick as the rest of the wall. Depressed annular surface 11 is entended as a sort of a flexible diaphragm that, although it is integral with the wall of the container, can move elastically in relation to the rest of the wall. There is a groove 13 formed in the center of the inside of circular area 12. Annular surface 11, circular area 12, and groove 13 are intended to transmit to the liquid the ultrasonic vibrations generated by a transducer positioned against circular area 12 in order to agitate the liquid as a result of the cavitation thereby induced in it. It should be emphasized that the annular surface 11 is located in the vicinity of the apex of the angle between faces 7 and 8. This location is preferable in that it also helps prevent the establishment of dead zones in the only region of the liquid where the agitation could possibly be attenuated. Furthermore, once the particles have been collected in the area of wall face 8 adjacent to the obtuse angle and when they are to be resuspended, the ultrasound will be able to act directly on them and disperse them.

The outside diameter of the annular surface 11 in the illustrated embodiment is 6 mm and its inside diameter 2 mm.

The wall of the container is 0.8 mm thick and the annular surface 0.3 mm thick. The container is extruded of polystyrene or polyacralate.

Although the compartments 3 and 4 in the illustrated embodiment are in the shape of tubes with a rectangular cross-section, it will be obvious that the invention can also be unrestrictedly applied to tubes with a different cross-section, circular for example. The rectangular shape, however, will permit colorimetric measurements of the liquid, which is facilitated when the beam can pass through parallel surfaces.

Figure 3:
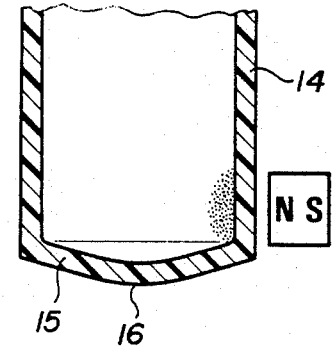
FIG. 3 is a section of the variant along a diameter thereof.

FIG. 3 illustrates a variant in which a tubular enclosure is used. In this variant, the enclosure bottom wall consists of a frustoconical portion 15 whose beveled angle is of about 120° and 150°. This frustoconical portion is terminated by a spherical cap 16 for ensuring a complete aspiration of the liquid phase, which operation would be more difficult if the bottom were conically shaped.

I claim:

1. A container especially adapted for use in a process for determining the quantity of antibodies or antigens in a biological liquid which process forms specific antibody-antigen complexes, one of said antigens or antibodies being initially associated with suspended magnetic particles, said complexes being separated from the remainder of a liquid sample by gathering them against a side wall of the container by magnetic attraction of said particles, said container comprising:
   a tubular body having an open upper end and a lower end closed by a bottom wall;
   said tubular body having a side wall having a collecting surface portion situated at a lower part of said side wall, said collecting surface portion being located above said bottom wall and being directly laterally accessible from the space surrounding said tubular body whereby a magnet may be placed adjacent said collecting surface;
   said bottom wall having a cross section which includes a curved portion defining an arc of a circle and a retaining surface portion located between said curved portion of said bottom wall and said collecting surface portion of said wall, said retaining surface portion being substantially planar and forming an angle with said collecting surface portion of substantially 105° to 120°.

2. A container according to claim 1, wherein said side wall is a first side wall and the tubular body has a rectangular cross-section, said retaining surface portion being located adjacent said side wall of the container and being tangent to said arc defined by said curved portion of said bottom wall, said arc being itself tangent to a second side wall of the said container which is opposite to said first side wall which includes said collecting surface portion.

3. The combination of the container of claim 1 and a magnet, said magnet being located adjacent said collecting surface portion of said side wall.

4. A container especially adapted for use in a process for determining the quantity of antibodies or antigens in a biological liquid which process forms specific antibody-antigen complexes, one of the antigens or antibodies being initially associated with suspended magnetic particles, the complexes being separated from the remainder of a liquid sample by gathering them against a side wall of the container by magnetic attraction of the particles, said container comprising:
   a tubular body having a rectangular cross-section, and an openupper end and a lower end closed by a bottom wall;
   said tubular body having first and second side walls, said first side wall having a collecting surface portion situation at said first side wall, said collecting surface portion being located above said bottom wall;
   said bottom wall having a cross section which includes a curved portion defining an arc of a circle and a retaining surface portion located between said curved portion of said bottom wall and said collecting surface portion of said first side wall, said retaining surface portion being substantially planar and forming an angle with said collecting surface portion of substantially 105° to 120°, said retaining surface portion positioned adjacent said first side wall of said container and being tangent to said arc defined by said curved portion of said bottom wall, said arc being itself tangent to said second side wall of said container, which is opposite to said first side wall; and a partition extending between said first and second side walls from said bottom wall to said upper end and positioned and arranged to divide said container into two identical compartments.

5. A container especially adapted for use in a process for determining the quantity of antibodies or antigens in a biological liquid which process forms specific antibody-antigen complexes, one of the antigens or antibodies being initially associated with suspended magnetic particles, the complexes being separated from the remainder of a liquid sample by gathering them against a side wall of the container by magnetic attraction of said particles, said container comprising:

a tubular body having an open upper end and a lower end closed by a bottom wall;

said tubular body having a side wall having a collecting surface portion situated at a lower part of said side wall, said collecting surface portion being located above said bottom wall, said collecting surface being less rigid than the rest of said side wall and being elastically connected to the rest of said side wall; and said bottom wall having a cross section which includes a curved portion defining an arc of a circle and a retaining surface portion located between said curved portion of said bottom wall and said collecting surface portion of said side wall, said retaining surface portion being substantially planar and forming an angle with said collecting surface portion of substantially 105° to 120°.

* * * * *